Figure 1:
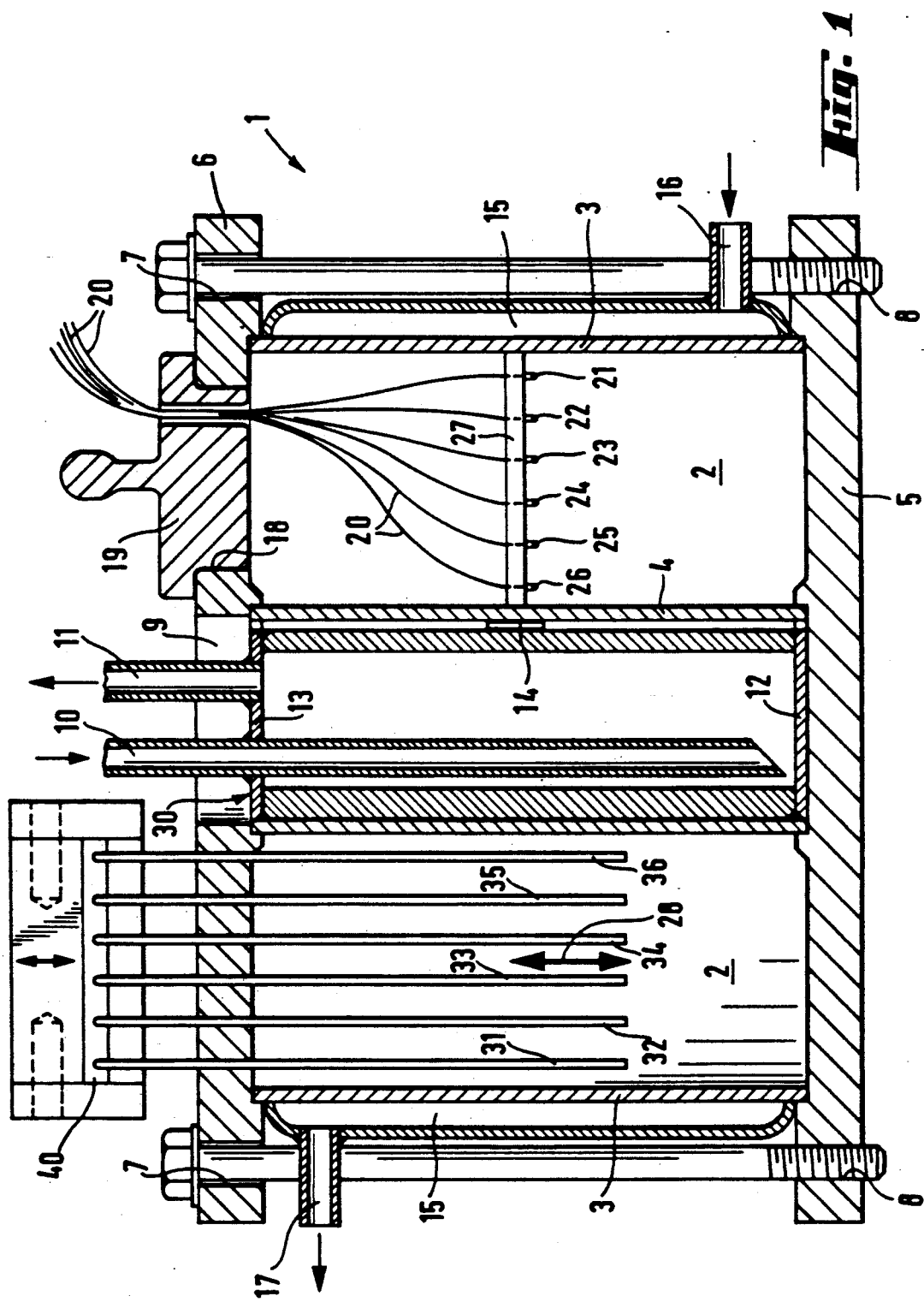

United States Patent [19]

Munk et al.

[11] Patent Number: 5,194,197

[45] Date of Patent: Mar. 16, 1993

[54] METHOD OF CHECKING THE GELLING PROCESS AFTER POURING A REACTIVE RESIN SYSTEM INTO A PRODUCTION MOULD

[75] Inventors: Kurt Munk, Grenzach, Fed. Rep. of Germany; Jürg Heizler, Basel, Switzerland

[73] Assignee: Ciba-Geigy Corporation, Ardsley, N.Y.

[21] Appl. No.: 712,851

[22] Filed: Jun. 10, 1991

[30] Foreign Application Priority Data

Jun. 13, 1990 [CH] Switzerland ............. 1986/90
Aug. 27, 1990 [CH] Switzerland ............. 2764/90

[51] Int. Cl.$^5$ .................. B29C 45/00; G01N 25/02
[52] U.S. Cl. .................. 264/40.1; 73/64.41; 264/40.6; 264/310; 264/328.1; 374/23; 374/25; 374/53; 425/143; 425/144
[58] Field of Search ............. 264/40.6, 40.1, 40.4, 264/328.1, 310, 40.5; 425/135, 140, 141, 143, 144, 149; 73/64.1; 374/16, 21-25, 45, 53

[56] References Cited

U.S. PATENT DOCUMENTS

| | | | |
|---|---|---|---|
| 2,423,687 | 7/1947 | Davis et al. | 374/23 |
| 3,718,721 | 2/1973 | Gould et al. | 264/40.6 |
| 3,747,397 | 7/1973 | Sharabash | 73/64.1 |
| 4,371,483 | 2/1983 | Mattson | 264/40.6 |
| 4,484,821 | 11/1984 | Willcock | 374/24 |
| 4,542,466 | 9/1985 | Arimatsu | 264/40.6 X |
| 4,589,072 | 5/1986 | Arimatsu | 264/40.6 X |
| 4,663,169 | 5/1987 | Hori et al. | 374/16 X |
| 4,810,438 | 3/1989 | Webster et al. | |
| 4,819,177 | 4/1989 | Jurgensen | 264/40.6 X |
| 4,828,472 | 5/1989 | Itoh et al. | |
| 4,869,098 | 9/1989 | Haakana | 73/64.1 |
| 4,911,629 | 3/1990 | Fujita | 264/40.6 X |
| 4,971,451 | 11/1990 | Hori et al. | 374/25 X |
| 4,983,336 | 1/1991 | Langlois | 264/40.6 X |
| 5,017,315 | 5/1991 | Kumazaki | 264/40.6 X |
| 5,055,245 | 10/1991 | Hisatomi et al. | 264/40.6 |
| 5,064,585 | 11/1991 | Cooper et al. | 264/40.6 |

FOREIGN PATENT DOCUMENTS

| | | |
|---|---|---|
| 0259252 | 3/1988 | European Pat. Off. |
| 333456 | 9/1989 | European Pat. Off. |
| WO/9104487 | 4/1991 | PCT Int'l Appl. |
| 798573 | 7/1958 | United Kingdom . |

OTHER PUBLICATIONS

"D2471 Gel Time and Peak Exothermic Temperature of Reacting Thermosetting Resins", Injection Molding Handbook, edited by Rosato and Rosato, Van Nostrand Reinhold Company, Inc., 1986, p. 716.

Mitsui Kensetsu KK, Derwent Abstract No. 84-149677 (JP-A-59078988).

*Primary Examiner*—Karen Aftergut
*Attorney, Agent, or Firm*—Harry Falber; Luther A. R. Hall; JoAnn Villamizar

[57] ABSTRACT

In a method of checking the gelling process after pouring a reactive resin system into a production mould, the gelling behavior of a resin system is detected by means of calibration measurements and stored. Temperature patterns of the resin system are detected and, for each temperature pattern, the temperature at which the gelling point lies is determined. A scalar value and the gelling moment temperature are associated with each temperature pattern. On carrying out a checking measurement inside a production mould, the temperature patterns at various sites inside the production mould are detected using a large number of thermocouples. Scalar values are obtained from the temperature patterns and are compared with the scalar values established during the calibration measurement in order to establish gelling moment temperatures. The particular advantage of the method described is that the checking measurement of a production mould requires the use only of thermocouples and not of gelling point probes.

7 Claims, 6 Drawing Sheets

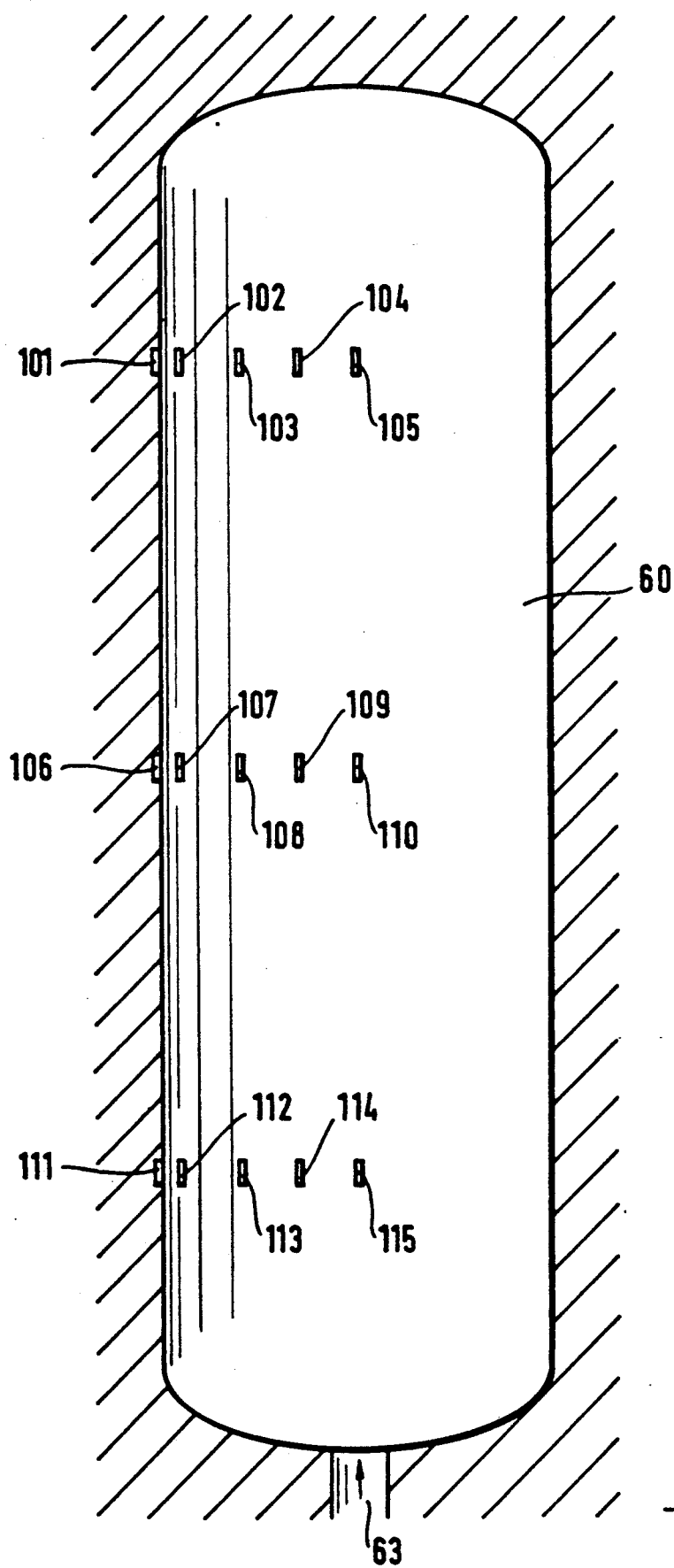

METHOD OF CHECKING THE GELLING PROCESS AFTER POURING A REACTIVE RESIN SYSTEM INTO A PRODUCTION MOULD

The invention relates to a method of checking the gelling process after pouring a reactive resin system into a production mould.

The principle of the pressure gelling process is known from application examples for Araldite, No. 39, "Das Druckgelierverfahren-eine rationelle Giesstechnik zur Herstellung von Epoxidharz-Formstoffen" ("The pressure gelling process—an efficient casting technique for the production of epoxy resin mouldings") of Ciba-Geigy AG, Plastics and Additives Division, Basle, May 1972. When a reactive resin system hardens, an exothermic chemical reaction, associated with an increase in temperature, and a reaction shrinkage of the volume of the hardening material take place during the gelling process, so that, depending on the spatial progress of the gelling process along one or more gelling fronts, in addition to the risk of uneven gelling and the local overheating thereby caused, there is a risk that voids will be formed as a result of the great decrease in volume during solidification when the outer zones of a volume have solidified completely but resin that has not yet solidified is present in the core zone of the volume. Such defects can occur in the pressure gelling process, in spite of the efficient control and checking of the progress of the reaction, if the production mould has a geometrically or thermally unfavourable structure.

An attempt has already been made to simulate the progress of the solidification front of rapid-hardening epoxy resins and similar materials using a computer programme (Erich Knauder, thesis, Montanuniversitat Leoben, Austria, Feb. 6, 1989). This and other computer programmes, however, give results that in practice do not yet meet accuracy requirements.

In order to ascertain the gelling behaviour over time of a reactive resin system, it is also already known to use mechanical gelling point probes in the case of which a pin immersed in the resin and moved up and down until the latter has hardened emits a signal when the gelling point is reached (TECAM measuring apparatus). When such a measuring apparatus is used to check the gelling process in a production mould, however, interference effects are produced so that it is no longer possible to detect the true progress of the gelling front or solidification front in the production mould.

The problem of the invention is to provide a method that permits the highly accurate three-dimensional recording, as a function of time, of the spatial migration of the gelling front during the hardening process in a production mould provided for the manufacture of a large number of castings.

That problem is solved according to the invention by ascertaining, in a calibrating mould that can be heated to various predetermined temperatures, during a calibration measurement, the gelling behavior of the resin system provided for the manufacture of the casting. This is accomplished by detecting, at various calibrating mould temperatures, after introducing the resin system into the calibrating mould and using gelling point probes, the moment of gelling of several volume elements which have different gelling behaviors and are located inside the calibrating mould and by detecting, using temperature sensors, the associated temperature patterns over time from the moment at which the resin system is introduced into the calibrating mould up to the maximum temperature occurring at the peak of the exothermic reaction after the moment of gelling. The gelling moment temperatures determined are stored and there is established an associated characteristic scalar value for each temperature pattern by determining and storing the calibration volume of an associated comparison body the base of which is established by the temperature pattern over time between the minimum and the maximum temperature of the resin system in the calibrating mould. The height of the comparison body is established by a gelling factor that changes in the direction of the temperature axis of the temperature pattern, which factor corresponds to the reciprocal of the gelling time at the temperature concerned. During a checking measurement, at several different measuring sites inside the production mould, under production conditions in the production mould provided and using embeddable temperature sensors, the temperature patterns over time of the resin system used in the calibration are detected and stored. There is then determined, for the so determined temperature patterns between the minimum and the maximum temperatures of the resin system, at the particular measuring sites, the measured volumes of associated comparison bodies, the base of which is established by the temperature pattern over time between the minimum and the maximum temperature of the resin system in the production mould and the height of which is established by the gelling time factor. The measured volumes of the comparison bodies, which volumes are determined for the different measuring sites inside the production mould, are compared with the calibration volumes of the comparison bodies, which volumes are stored together with the gelling moment temperatures. There is then determined, for the different measuring sites in the checked production mould, by interpolating the measured volumes between the stored calibration volumes, the associated interpolated individual gelling moment temperatures. From this on the basis of the stored temperature patterns over time detected in a spatially distributed manner, and on the basis of the pattern of the isotherms resulting therefrom, the progress of the gelling front in the production mould, which front intersects the isotherms, is deduced for each point in time.

Since the passage of a gelling front is detected not mechanically but, according to the invention, thermally, it is possible, using thermocouples arranged in a spatially distributed manner in a production mould to be checked, to detect not only the thermal event spatially and in time but also, from the migration over time of isotherms, taking into account measured gelling moment temperatures, the spatial progress of gelling fronts and accordingly the hardening process in an actual production mould. The thermocouples to be accommodated at various sites in the production mould are connected by thin wires, which impair neither pouring nor hardening, to a device for detecting, storing and evaluating temperature patterns over time.

An embodiment of the invention is described in detail hereinafter with reference to the drawing.

Figure 2:
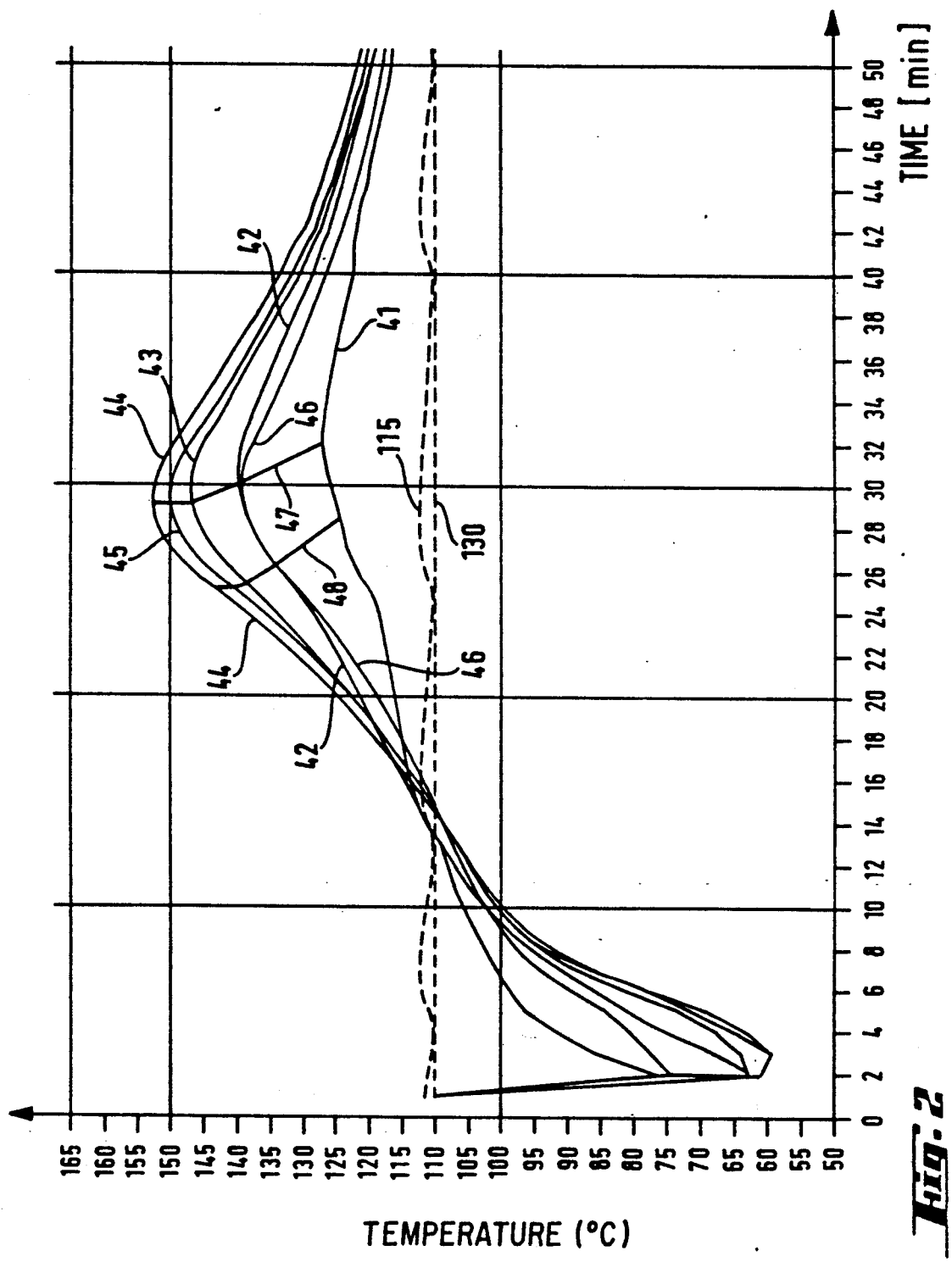
Figure 3:
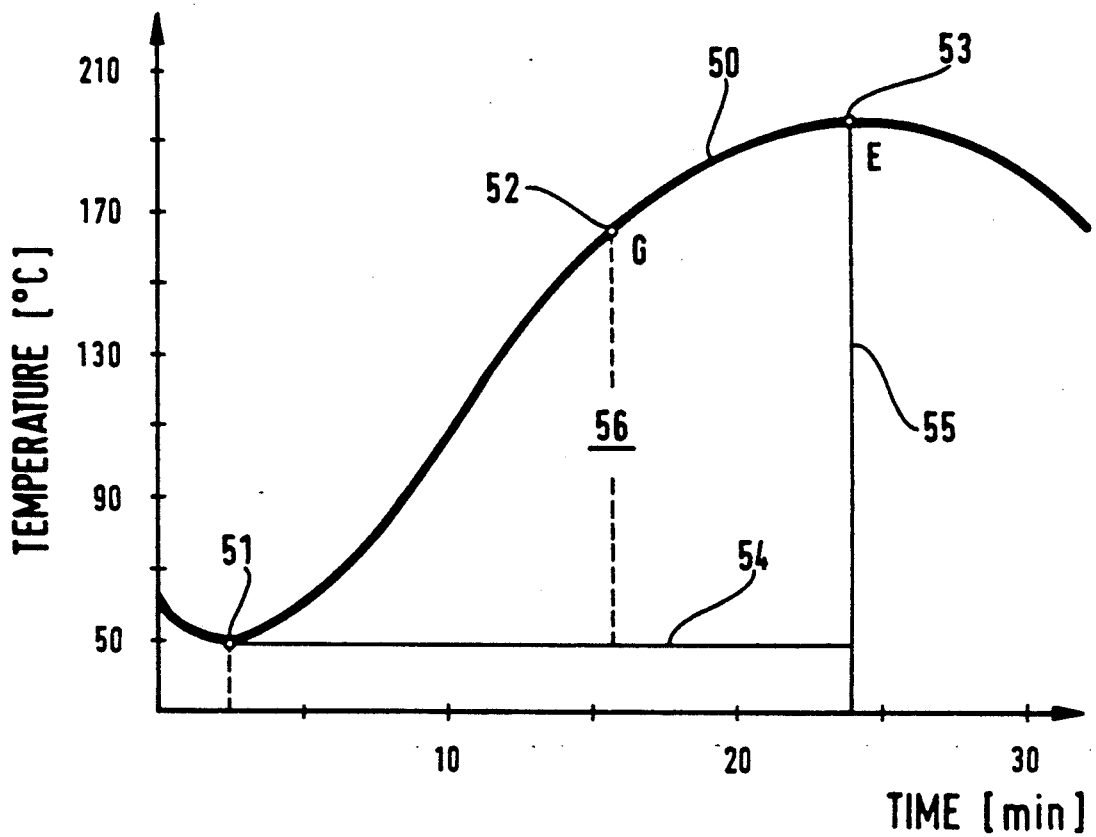

FIG. 1 shows a longitudinal section through a calibrating mould for carrying out calibration measurements on resin systems at various temperatures, FIG. 2 shows temperature patterns, detected by temperature sensors arranged at six different sites in the calibrating mould, from the moment of introducing the resin system into the calibrating mould up to a point in time after the peak of the exothermic reaction, FIG. 3 shows a schematic representation of an individual temperature pattern corresponding to FIG. 2.

Figure 4:
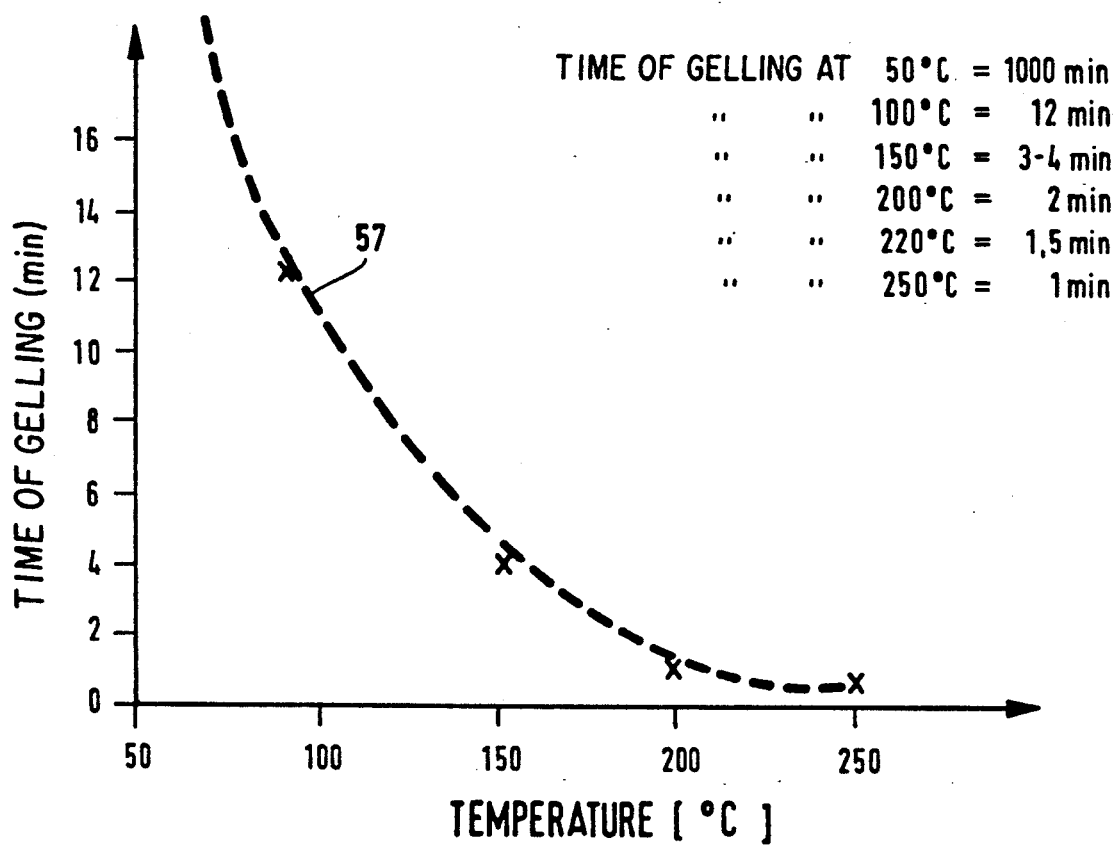
Figure 5:
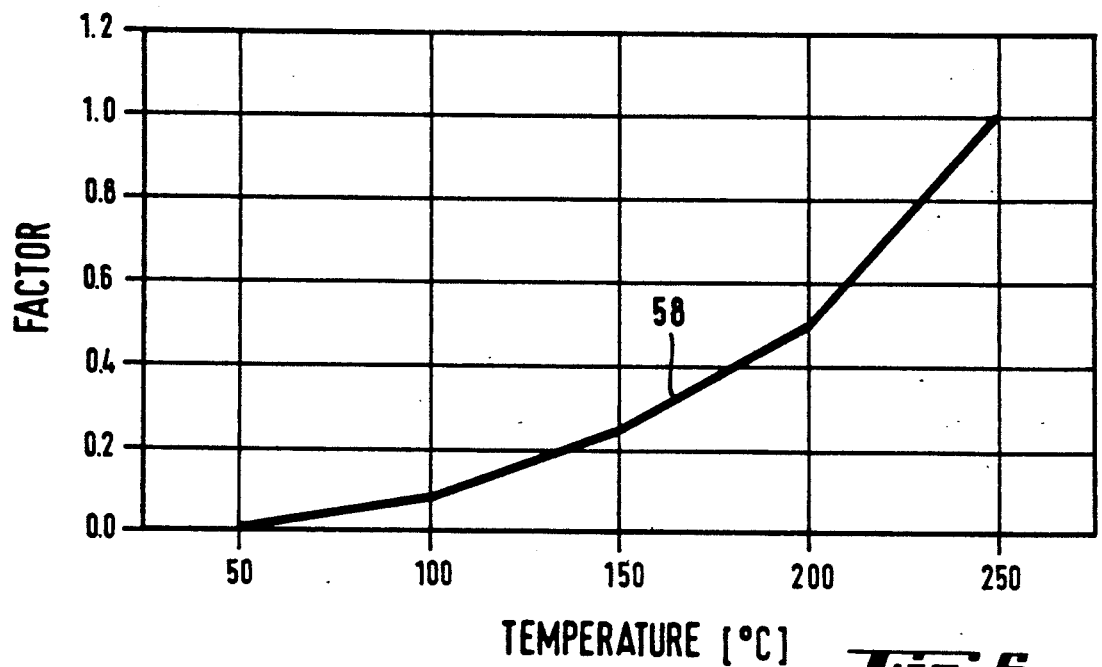
Figure 6:
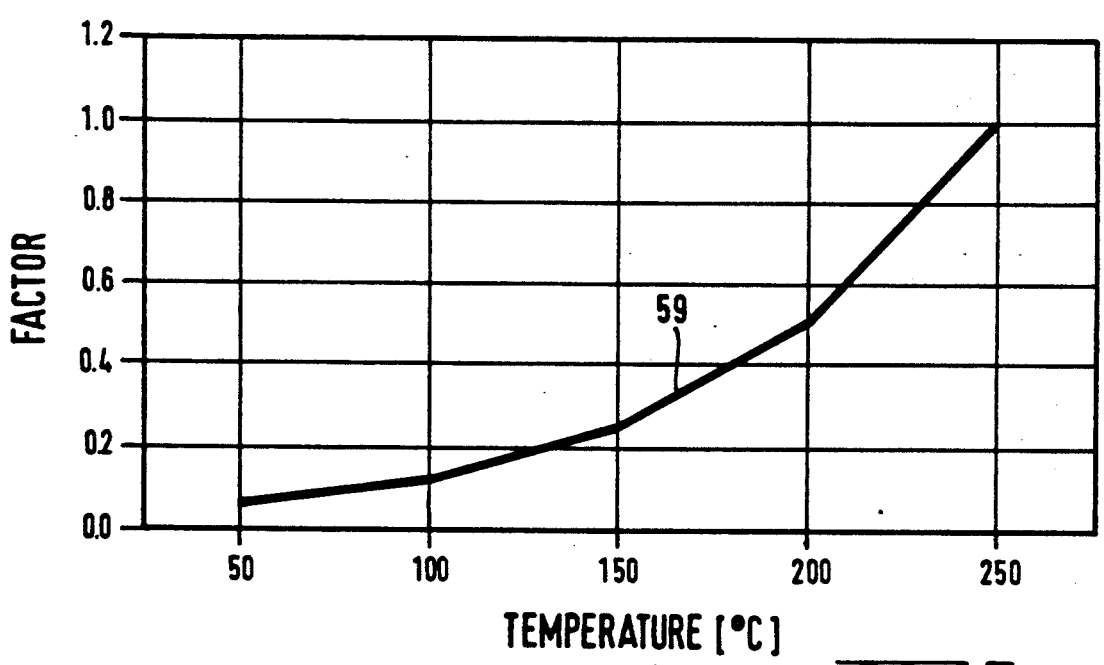

FIG. 4 shows the gelling time of a resin system as a function of the temperature of the resin system, FIG. 5 shows the pattern of a gelling time factor which corresponds to the reciprocal of the gelling time at the temperature concerned, FIG. 6 shows the pattern of an approximated gelling time factor in dependence on the temperature and FIG. 7 shows a diagrammatic representation of a heatable casting mould to illustrate the spatial arrangement of a large number of temperature sensors during a checking measurement in a production mould.

FIG. 1 shows a longitudinal section through a calibrating mould 1 for carrying out calibration measurements on resin systems at various temperatures. The calibrating mould 1 has a rotationally symmetrical preheated mould cavity 2 into which a prepared casting resin mixture, especially a resin system based on epoxy resin with a quartz powder as filler, can be introduced. The mould cavity 2, which is shown in longitudinal section in FIG. 1, has an annular shape in cross-section at right angles to the plane of FIG. 1, the mould cavity 2 being delimited along the larger circumference by a cylindrical outer wall 3 and along the smaller circumference by a cylindrical inner wall 4. The cylindrical walls 3 and 4, which are formed by tubular members, are closed by a base plate 5.

On the side opposite the base plate 5, the annular mould cavity 2 is closed by a cover plate 6. Distributed over the circumference of the cover plate 6, which is circular in plan view, are fastening holes 7 through which fastening screws can be pushed, the front ends of which can be screwed into associated fastening threads 8 in the base plate 5 and the heads of which hold the cover plate 6 and the base plate 5 together.

Also arranged in the round cover plate 6 is a concentric opening 9 through which an oil inlet tube 10 and an oil outlet tube 11 project into a cylindrical heating cartridge 30 arranged inside the cylindrical inner wall 4, which cartridge 30 is closed on its underside by a base disc 12 and on its upper side by a cover disc 13.

Oil heated to a predetermined temperature for heating the calibrating mould 1 is introduced into the heating cartridge 30 through the oil inlet tube 10, the front end of which projects down to the vicinity of the base disc 12 of the heating cartridge 30. The cooled oil leaves the heating cartridge 30, which is in contact with the inside of the cylindrical inner wall 4, through the oil outlet tube 11. A temperature sensor 14 arranged in a land of the cylindrical housing of the heating cartridge 30 enables the temperature at the heating cartridge 30 to be detected.

The cylindrical outer wall 3 is surrounded by a heating jacket 15 so that there is formed between the heating jacket 15 and the cylindrical outer wall 3 an annular space through which hot oil can likewise flow to heat the mould cavity 2. The oil used for heating passes through an inlet connecting piece 16 into the intermediate space between the heating jacket 15 and the outer wall 3 and leaves the intermediate space through an outlet connecting piece 17. The heating cartridge 30 and the heating jacket 15 enable the calibrating mould 1 to be heated to various predetermined temperatures for calibration purposes.

In order to be able to introduce a resin system such as epoxy resin or araldite into the mould cavity 2, there is provided in the cover plate 6 a filling opening 18, shown in section in FIG. 1, which can be closed by a covering 19.

Running through the covering 19 are a large number of connecting wires 20 which are connected to one another in pairs at their leading ends to form thermocouples 21, 22, 23, 24, 25 and 26. The thermocouples 21 to 26 are fixed in position by a spacing means 27 along a radius of the mould cavity 2 approximately in the axial centre of the mould cavity 2 in the axial direction and permit the detection of temperature patterns at the respective sites inside the mould cavity 2, and accordingly inside a hardening resin system, from the moment of introducing the resin system into the mould cavity 2 serving as a calibrating mould up to the maximum temperature at the peak of the exothermic reaction occurring after the moment of gelling.

Arranged diametrically opposite the thermocouples 21 to 26 are small glass tubes 31 to 36 that can be moved up and down in the direction of the double arrow 28. The small glass tubes 31 to 36 and the thermocouples 21 to 26 each lie on concentric circles around the inner wall 4 inside a cross-sectional plane which passes through the calibrating mould 1 and is at right-angles to the plane of the drawing. Owing to the rotational symmetry of the calibrating mould 1, therefore, the physical and especially the thermal conditions at the site of the thermocouple 21 are identical with those at the site of the small glass tube 31. The same applies to the thermocouple 22 and the small glass tube 32 and to the other thermocouples 23 to 26 and small glass tubes 33 to 36. Thus, the thermocouples 21 to 26, which are separated spatially from the small glass tubes 31 to 36, permit accurate detection of the temperatures at the sites of the small glass tubes 31 to 36 in order to ascertain the temperature at the moment of gelling.

The ends of the small glass tubes 31 to 36 immersed in the resin system cease to move up and down when the resin system in which they are immersed hardens at those particular sites, the small glass tubes 31 to 36 breaking off in the vicinity of a holding member 40. FIG. 1 shows the holding member 40 for the small glass tubes 31 to 36 which on the one hand enables the vertical movement necessary for the gelling time measurement to be imparted to the small glass tubes 31 to 36 and, on the other hand, enables the breaking off of a small glass tube 31 to 36 as the gelling front passes through to be detected using contact device (not shown). Thus, when, for example, the gelling front in the radial direction passes the small glass tube 31 and the latter is held fast by the hardening resin, a corresponding signal is emitted by means of the holding member 40 so that the gelling time temperature just detected by the symmetrically arranged thermocouple 21 can be associated as the gelling moment temperature with the gelling moment so detected.

The calibrating mould 1 with the gelling point probes formed by the small glass tubes 31 to 36 and the associated mechanics and evaluating device, together with the thermocouples 21 to 26, accordingly permit the detection of temperature patterns at various sites inside the mould cavity 2 for different oil temperatures and, for each temperature pattern detected, permit the accurate determination of the gelling moment temperature at different sites, that is to say, for several volume elements in the calibrating mould 1. Such calibration measurements give, for a specific resin system in each case, calibration data that later enable the migration over time of the gelling front to be determined in any production mould merely by temperature measurements.

FIG. 2 shows an example of six temperature patterns 41 to 46 which were detected using the thermocouples 21 to 26 for a specific resin system at a temperature of the calibrating mould 1 of 110° C. The pattern of the regulated heating jacket temperature is provided with the reference numeral 115 and the pattern of the heating cartridge temperature is provided with the reference numeral 130. As shown in FIG. 2, the temperature falls at the sites of the thermocouples 21 to 26 to values in the range of from 60° to 80° C. within approximately two minutes after the introduction of the resin system and then rises as a result of heating the originally cold resin system and as a result of the heat of reaction released during hardening to maximum temperatures or peaks of exothermic reaction, which are connected to one another in FIG. 2 by an exothermic reaction line 47.

The gelling point probes formed using the small glass tubes 31 to 36 permit the detection and indication of the gelling moments on the temperature patterns 41 to 46. In FIG. 2 the gelling moments are connected to one another by a gelling moment line 48. It can be seen that the gelling front passes through the calibration measuring sites of the thermocouples 21 to 26 and of the small glass tubes 31 to 36 within a period of approximately from 25 to 28 minutes after introducing the cold resin system. Depending on the radial position of the observed volume element around one of the thermocouples 21 to 26, the exothermic peak occurs only after approximately from 29 to 32 minutes, as can be seen from FIG. 2. The associated gelling moment temperatures and exothermic peak temperatures can also be found in FIG. 2 and, depending on the volume element measured, are at approximately from 124° to 153° C.

FIG. 3 shows in a greatly schematisised amnner and by way of example a temperature pattern 50 such as is known from FIG. 2 and can be detected by the thermocouples 21 to 26 in the case of a specific volume element. The temperature pattern 50 illustrates the pattern over time of the temperature of a resin system measured by one of the thermocouples 21 to 26 in the calibrating mould 1, which resin system first cools the preheated calibrating mould 1 after being introduced until a minimum temperature 51 is reached after approximately from 2 to 3 minutes in the case of the example shown in FIG. 3. On reaching the minimum temperature 51, the temperature of the resin system introduced into the calibrating mould 1 begins to increase, this increase being caused especially by exothermic heating. During exothermic heating, the temperature detected by one of the thermocouples 21 to 26 increases in the manner shown in FIG. 3 until the gelling point G, indicated by the reference numeral 52, of the volume element concerned is reached and measured. On reaching the gelling point 52, the gelling point 52 is detected in terms of time by means of the gelling point probe containing the small glass tubes 31 to 36. FIG. 3 shows that, in the case of the example illustrated there, the gelling point is reached after approximately 16 minutes at a temperature of approximately 170°. The coordinates of the gelling point 52 in the coordinate system shown in FIG. 3 give the gelling moment and the gelling moment temperature of a volume element around the thermocouple of a resin system.

During a calibration measurement using the calibrating mould 1, the temperature pattern 50 is stored in an evaluating unit, for example a computer, not shown in the drawing. When the gelling point 52 is reached, the computer receives a signal via the gelling point probe, which has the small glass tubes 31 to 36 and is associated with the thermocouple 21 to 26 concerned, so that, in addition to the temperature pattern 50, the coordinates of the gelling point G provided with the reference numeral 52 in FIG. 3 can also be stored. Of particular importance for further evaluation of the temperature pattern 50 is the gelling moment temperature, which is approximately 170° C. in the embodiment shown in FIG. 3.

As shown in FIG. 3, the temperature of the resin continues to rise after the gelling point 52 has been reached and finally reaches a maximum exothermic peak E provided with the reference numeral 53 in FIG. 3.

If a straight line is drawn through the minimum temperature point 51 parallel to the time axis of FIG. 3 and straight lines are drawn through the gelling point 52 and the exothermic peak 53 parallel to the temperature axis, then the area delimited by those straight lines under the curve of the temperature pattern 50 can be associated with the energy released up to the gelling moment 52 or with the energy released up to the exothermic peak 53. The total thermal energy released between the point in time of the minimum temperature 51 and the point in time of the exothermic peak 53 can thus be associated with the area that is delimited on the one hand by the line 54 parallel to the time axis and, on the other, by the line 55 parallel to the temperature axis and also by the curve of the temperature pattern 50. Depending on the form of the temperature pattern 50, that is to say, in accordance with the distance between the minimum temperature 51 and the exothermic peak 53 and also the necessary period of time between those two temperatures, the base 56, which can be determined in the manner described above, has different values.

For each of the temperature patterns 41 to 46 detected by the thermocouples 21 to 26, the base 56 is determined during the calibration measurement at different calibrating mould temperatures for a given resin system in accordance with the temperature pattern 50 discussed by way of example.

FIG. 4 shows in a gelling time curve 57, in the case of a resin system used by way of example, how the gelling time in minutes decreases as the temperature of the resin system or of the calibrating mould 1 increases. At a resin temperature of 100° C., the gelling time is, for example, 12 minutes, at 150° C. approximately 4 minutes, at 200° C. approximately 2 minutes and at 250° C. approximately 1 minute.

According to the present invention, a scalar value or coefficient of measure is determined e i on the basis of the temperature pattern 50 by determining the calibration volume of a comparison body, the base of which is the base 56 shown in FIG. 3 and the height of which, increasing in the direction of the temperature axis, corresponds to the reciprocal of the gelling time curve 57 shown in FIG. 4. That provides a weighing of the base 56 in accordance with the reactivity or the gelling time of a resin as a function of the temperature.

FIG. 5 shows a gelling factor curve 58 that is obtained by forming the reciprocal value from the gelling time curve 57. The gelling factor curve 58 represents the height of the comparison body above the base 56 in FIG. 3 along the temperature axis. The calibration volume of the comparison body formed on the base 56 accordingly depends to only a slight degree on the temperature pattern 50 at low temperatures owing to the lower height there, but depends very greatly on the temperature pattern 50 at higher temperatures since in that region the comparison body is very high in the direction of the axis running at right-angles to the temperature axis and time period axis in FIG. 3. That height is represented by the pattern of the gelling factor curve 58 in FIG. 5.

The above shows that, with the aid of a computer programme, it is readily possible on the basis of a temperature pattern 50, which represents, for example, one of the temperature patterns 41 to 46, to establish a scalar value that has been designated as the calibration volume of a comparison body associated with a temperature pattern 50.

According to the invention, for a specific resin system, at a large number of temperatures of the calibrating mould 1, using the thermocouples 21 to 26, a large number of temperature patterns 50 are obtained for a large number of different volume elements, which patterns are evaluated by a time integral over temperature forming a base 56. In a further step, an area curved in the direction of the temperature axis of FIG. 3 is set above the base 56 in accordance with the curve shown by the gelling factor curve 58 in FIG. 5 so that this area above the base 56 delimits a comparison body, the calibration volume of which can be associated with the entire thermal energy released.

During the calibration measurement, a large number of comparison body calibration volumes are established in the manner described above. Each calibration volume represents a scalar value that characterises the particular comparison body associated with the temperature curve 50. The temperature of the gelling point 52, which temperature is indicated by the gelling point probe, is also associated with each of the comparison body calibration volumes so established. The computer evaluating the data obtained in the calibrating mould 1 thus produces for each resin system subjected to calibration a list having two columns, the calibration volumes of all detected temperature patterns 50 being indicated in the first column and the associated gelling moment temperatures being indicated as the second scalar value of calibration pairs in the second column.

The present invention is based on the recognition that it is possible, in the manner described above, to form characteristic scalar values which have been designated as calibration volumes of comparison bodies with which gelling moment temperatures can be associated in an unequivocal manner. When in the case of a given resin system the above-mentioned pairs of figures, constituted by the calibration volume and the gelling moment temperature, are recorded on the basis of a calibration measurement, it is possible to establish on the basis of a measurement of the temperature pattern of the resin inside another mould the gelling moment temperature on the basis of the above-mentioned table by detecting the temperature pattern 50 between the minimum temperature 51 and the exothermic peak 53 and determining from that temperature pattern 50 the measured volume of a comparison body analogously to the manner mentioned above. If the comparison body volume determined in that manner occurs in the table created during the calibration measurements, the table immediately gives information on the gelling moment temperature.

In a method that is somewhat simplified computationally, the pattern of the gelling factor curve 58 shown in FIG. 5 is replaced by a gelling factor curve 59 that has been determined computationally by increasing the gelling factor by 1.395947979% for each degree of temperature increase, the gelling time factor for 1° C. being $3.16862337434.10^{-2}$. Such a calculation gives, for 50° C., a gelling time factor of 0.0625, for 100° C. a gelling time factor of 0.125, for 150° C. a gelling time factor of 0.25, for 200° C. a gelling time factor of 0.5 and for 250° C. a gelling time factor of 1. As already mentioned, those factors give the height of the comparison body above the base 56 in FIG. 3 in the direction of a coordinate axis perpendicular to the axes shown in FIG. 3.

When the calibration measurements discussed above have been completed for a resin system that is to be used to manufacture a moulding, for example an electrically insulating component, in a production mould in the pressure gelling process, a production mould can be used that has, for example, the casting form shown in FIG. 7. The invention enables the progress of the gelling front in a production mould shown as an example in FIG. 7 to be measured by detecting and evaluating only temperature patterns 50 of the type shown in FIG. 3. Mechanical gelling moment probes as were used for calibration measurement in the calibrating mould are not necessary for a checking measurement under production conditions in the production mould provided.

FIG. 7 shows diagrammatically a cross-section through a cylindrical production mould 60 that has, for example, a diameter of 60 mm and a length of 180 mm. At the sites marked by short lines, a large number of spatially distributed thermocouples 102 to 115 corresponding to the thermocouples 21 to 26 are arranged in the production mould 60.

As shown in FIG. 7, the thermocouples 102 to 105 are arranged in an upper plane and the thermocouples 107 to 110 and the thermocouples 112 to 115 are arranged in a lower plane. There is also a further thermocouple 101, 106, 111 in each plane that permits the detection of the temperature directly at the wall of the production mould 60.

At the bottom of FIG. 7 can be seen a feed head 63 through which, in order to carry out a checking measurement in accordance with the pressure gelling process, a resin system can be introduced for which calibration measurements have been carried out beforehand. As soon as the production mould 60 has been filled with resin, the thermocouples 102 to 115 detect temperature patterns corresponding to the temperature pattern 50 and transmit them by way of lines (not shown in the drawing) to a computer which first of all records all of the temperature patterns 50 supplied by the thermocouples 102 to 115. Once the temperature patterns 50 between the minimum temperature 51 and the exothermic peak 53 are available, a programme stored in the computer calculates the volume, which may be designated a measured volume, of a comparison body having the base 56 and a height that is defined in the manner described above by the inverse gelling times.

When, for each temperature pattern 50 that has been detected by the thermocouples 102 to 115, the scalar value designated as a measured volume of a comparison body is established, it is readily possible for the computer to establish the gelling moment temperature at the sites of the thermocouples 102 to 115. That is effected in a simple manner by comparing the measured volumes of the comparison bodies established during the checking measurement of the production mould 60 with the previously established calibration volumes that are stored in the form of a table in the computer's memory. In the simplest case it will be found that the scalar value of the measured volume occurs as a calibration volume in the table of the computer. The associated gelling moment temperature is deduced directly from the temperature associated with the stored calibration volume. If the value of a measured volume established during the checking measurement of a production mould 60 does not coincide with a calibration volume present in the computer's memory, then a linear interpolation is effected by means of the computer which uses the calibration volumes above and below the measured volume established on checking the production mould 60 in order to calculate from the two gelling moment temperatures associated with the adjacent calibration volumes a gelling moment temperature that is an interpolated value for the measured volume falling between two calibration volumes.

The invention thus first enables a comparison body having a measured volume to be associated with each temperature pattern 50 detected by the thermocouples 102 to 115 and then enables a direct or interpolated gelling moment temperature to be found in the table of calibration volumes and gelling moment temperatures, which gelling moment temperature applies to the volume element in the vicinity of the particular thermocouple 102 to 115. If the temperature patterns measured in the production mould are in graphic form, it is accordingly possible to indicate the gelling moment temperature for each of those temperature patterns 50.

By evaluating the temperature patterns 50 for the thermocouples 102 to 115, it is accordingly possible on the one hand to provide at the site of each thermocouple a temperature profile over time, with the gelling point being indicated. It is also possible as a result of knowing the temperature at the thermocouples 102 to 115 to show the spatial temperature pattern and isotherms for a production mould. The accuracy of the isotherms is the greater the more numerous and more skillfully distributed are the thermocouples 102 to 115 in the production mould.

Since, for the resin volume that surrounds any one of the thermocouples 102 to 115, it is possible in the manner described above to establish the gelling moment temperatures by way of the detected measured volumes by referring to the table of calibration volumes and associated gelling moment temperatures, the invention makes it possible to indicate not only the pattern of the isotherms inside the production mould at different times but also the progress of the gelling front at different times during the hardening process. If in the region of a thermocouple 102 to 115 the individual gelling moment temperature established in the manner described above by evaluating the temperature pattern 50 is reached exactly, that thermocouple 102 to 115 lies exactly in the gelling front. If the temperature is higher, the gelling front has already passed. If the temperature is lower, then the thermocouple 102 to 115 is still in unhardened resin.

Associated with the computer for evaluating the temperature patterns 50 supplied by the thermocouples 102 to 115 is a graphic indicator unit that enables the outline of the production mould and the position of the particular thermocouples 102 to 115 used to be represented. In addition to indicating the position of the thermocouples 102 to 115, the graphic indicator unit enables the thermal distribution along a section through the production mould to be represented by colours and isotherms. The graphic indicator unit also permits the indication of the progress of the gelling front as a function of time and the progress of the exothermic front as a function of time.

Since the progress of the gelling fronts in the production mould is the decisive criterion for the quality of a casting, it is desirable to avoid gelling fronts that move too fast, or that move unevenly or that merge, because they lead to local peaks of exothermic reaction, to the formation of voids and to centres of tension. Owing to the invention, the progress of the gelling fronts can be spatially detected and represented. If they are unfavourable, they can be influenced by changing various parameters. Those parameters are the temperature of the resin system, the temperature of the production mould and the reactivity of the casting resin material.

The above-described method according to the invention is especially suitable for use in the manufacture of large-volume castings in accordance with the pressure gelling process but is not in any way limited thereto. For example, it can also be used with excellent results, inter alia, in connection with the manufacture described, for example, in EP-A-0333456 of thin-walled castings of relatively large dimensions.

What is claimed is:

1. A method of determining a gelling process of a reactive resin system poured into a production mould for manufacture of a casting, which comprises:
   (i) ascertaining in calibration measurements a gelling behavior of said resin system provided for the manufacture of said casting prior to pouring it into said production mould,
      by pouring an amount of said resin system into a calibrating mould which is heatable to various predetermined calibrating mould temperatures:
      by detecting at various of said calibrating mould temperatures, using gelling point probes, moments of gelling of several volume elements which display different gelling behaviors and are located inside said calibrating mould;
      by detecting, using temperature sensors, associated first temperature versus time curves at various of said calibrating mould temperatures from a moment at which
      said resin system is introduced into said calibrating mould up to a maximum temperature occuring at a peak of an exothermic reaction after said moments of gelling;
      by storing said first temperature versus time curves measured and respective temperatures associated with said moments of gelling and by determining and storing an associated calibration volume of a first comparison body associated with each of said first temperature versus time curves,
         wherein each of said associated calibration volumes is defined as a product of a base area and a height of said first comparison body, said base area being an area between said respective first temperature versus time curve and a parallel to a time axis through a minimum temperature, within boundaries of said minimum temperature and said maximum temperature of said respective first temperature versus time curve, and said height corresponds to a gelling factor that changes in a direction of a temperature axis of said first temperature versus time curve, said gelling factor corresponding to a reciprocal of a gelling time at a temperature concerned;

(ii) pouring said resin system with thus ascertained gelling behavior into said production mould for the manufacture of said casting;

(iii) accomplishing a checking measurement during a hardening reaction of said resin system within said production mould while manufacturing said casting, by detecting at several different measuring sites inside said production mould, under production conditions and using embeddable temperature sensors, second temperature versus time curves of said resin system poured into said production mould;

by storing said second temperature versus time curves measured and by determining and storing for each of said second temperature versus time curves determined at said several measuring sites within said production mould a measured volume of a second comparison body associated with said second temperature versus time curve, wherein each of said measured volumes is defined as a product of a base area and a height of said second comparison body, said base area being an area between said respective second temperature versus time curve and a parallel to a time axis through a minimum temperature within boundaries of said minimum temperature and a maximum temperature of said respective second temperature versus time curve, and said height corresponds to a gelling factor that changes in a direction of a temperature axis of said second temperature versus time curve, said gelling factor corresponding to a reciprocal of a gelling time at a temperature concerned;

(iiii) comparing and determined and stored measured volumes of said second comparison bodies, said measured volumes being determined for said different measuring sites inside said production mould, with said calibration volumes of said first comparison bodies, said calibration volumes being stored together with said gelling moment temperatures, and determining for said different measuring sites within said production mould, by interpolating said measured volumes between said stored calibration volumes, associated interpolated individual gelling moment temperatures, from which, on the basis of said stored second temperature versus time curves detected in a spatially distributed manner, and on the basis of a pattern of isotherms resulting therefrom, the progress in time of a gelling front of said hardening resin system and its spacial progress within said production mould, said gelling front intersecting said isotherms, is deduced for each point in time during the manufacture of said casting.

2. A method according to claim 1, wherein, during said calibration measurement, a hardening reaction of said resin system is carried out without excess pressure.

3. A method according to claim 1, wherein, during said detection of said second temperature versus time curves at said measuring sites inside said production mould, said hardening reaction is carried out with excess pressure in accordance with a pressure gelling process.

4. A method according to claim 1, wherein the progress of an exothermic front as a function of time is established from said second temperature patterns versus time curves detected in said spatially distributed manner.

5. A method according to claim 1, wherein a calibrating mould having a rotationally symmetrical mould cavity is used.

6. A method according to claim 1, wherein large-volume castings are manufactured in said production mould during said determination of said gelling process.

7. A method according to claim 1, wherein thin-walled castings are manufactured in said production mould during said determination of said gelling process.

* * * * *